(12) United States Patent
Goetz et al.

(10) Patent No.: US 10,895,546 B2
(45) Date of Patent: Jan. 19, 2021

(54) BIPOLAR ELECTRODE FOR THE IMPEDIMETRIC EXAMINATION AND MANIPULATION OF LIVING CELLS IN VITRO

(71) Applicants: Fraunhofer-Gesellschaft zur Foerderung der angewandten Forschung e.V., Munich (DE); Universitaet Regensburg, Regensburg (DE)

(72) Inventors: Christian Goetz, Regensburg (DE); Joachim Wegener, Regensburg (DE)

(73) Assignees: FRAUNHOFER-GESELLSCHAFT ZUR FOERDERUNG DER ANGEWANDTEN FORSCHUNG E.V., Munich (DE); UNIVERSITAET REGENSBURG, Regensburg (DE)

( * ) Notice: Subject to any disclaimer, the term of this patent is extended or adjusted under 35 U.S.C. 154(b) by 30 days.

(21) Appl. No.: 15/839,379

(22) Filed: Dec. 12, 2017

(65) Prior Publication Data

US 2018/0164238 A1 Jun. 14, 2018

(30) Foreign Application Priority Data

Dec. 13, 2016 (DE) .......................... 10 2016 224 865

(51) Int. Cl.
*G01N 27/04* (2006.01)
*H01B 5/14* (2006.01)
(Continued)

(52) U.S. Cl.
CPC .............. *G01N 27/04* (2013.01); *C12M 1/34* (2013.01); *G01N 27/30* (2013.01);
(Continued)

(58) Field of Classification Search
CPC .............. G01N 27/04; G01N 27/3273; G01N 33/4836; G01N 33/5005; G01N 27/30;
(Continued)

(56) References Cited

U.S. PATENT DOCUMENTS 4,194,670 A * 3/1980 Ichisaka .................. C25B 11/02
228/179.1
4,623,440 A * 11/1986 Cairns ..................... G01N 27/30
204/230.1
(Continued)

FOREIGN PATENT DOCUMENTS

WO 2013012498 A1 1/2013
WO 2016139566 A1 9/2016

OTHER PUBLICATIONS

Wegener, J. et al., "Electric Cell—Substrate Impedance Sensing (ECIS) as a Noninvasive Means to Monitor the Kinetics of Cell Spreading to Artificial Surfaces," Experimental Cell Research, vol. 259, No. 1, Aug. 25, 2000, 9 pages.
(Continued)

*Primary Examiner* — William H. Beisner
*Assistant Examiner* — Danielle B Henkel
(74) *Attorney, Agent, or Firm* — McCoy Russell LLP

(57) ABSTRACT

The present disclosure relates to a measuring device with a bipolar electrode array for the impedimetric analysis of adherent cells according to the ECIS principle (electric cells substrate impedance sensing). The measuring device comprises an electrode array which is adapted for being wetted with an electrolyte solution and adherently growing cells in order to perform impedimetric cell analyzes, characterized in that the electrode array comprises a bipolar electrode on a substrate, where the bipolar electrode is formed as a conductive path on the transparent substrate and has an inherent resistance between two connection points of the conductive path that is a multiple of the AC impedance of (Continued)

the electrolyte solution at 1 MHz, measured at the two connection points.

17 Claims, 3 Drawing Sheets

(51) Int. Cl.
    *G01N 33/483*     (2006.01)
    *G01N 33/50*     (2006.01)
    *G01N 27/30*     (2006.01)
    *G01N 27/327*     (2006.01)
    *C12M 1/34*     (2006.01)
    *H01B 1/12*     (2006.01)
    *H01B 1/08*     (2006.01)

(52) U.S. Cl.
CPC ..... *G01N 27/3273* (2013.01); *G01N 33/4836* (2013.01); *G01N 33/5005* (2013.01); *H01B 5/14* (2013.01); *H01B 1/08* (2013.01); *H01B 1/124* (2013.01); *H01B 1/127* (2013.01); *H01B 1/128* (2013.01)

(58) Field of Classification Search
CPC ........... C12M 1/34; C12M 27/30; H01B 5/14; H01B 1/08; H01B 1/124; H01B 1/127; H01B 1/128
See application file for complete search history.

(56) References Cited

U.S. PATENT DOCUMENTS

| | | | |
|---|---|---|---|
| 9,851,343 B2* | 12/2017 | Abdolahad | G01N 27/021 |
| 2004/0152067 A1* | 8/2004 | Wang | G01N 33/5005 |
| | | | 435/4 |
| 2006/0057771 A1* | 3/2006 | Kovacs | G01N 33/4836 |
| | | | 438/106 |
| 2019/0178807 A1* | 6/2019 | Bohn | G01N 27/305 |

OTHER PUBLICATIONS

Kim, J. et al., "A multi-channel electroporation microchip for gene transfection in mammalian cells," Biosensors and Biolectronics, vol. 22, No. 12, Jun. 15, 2007, Published Online Feb. 16, 2007, 5 pages.

Granot, Y. et al., "Methods of optimization of electrical impedance tomography for imaging tissue electroporation," Physiological Measurement, vol. 28, No. 10, Sep. 18, 2007, 13 pages.

Wu, M. et al., "Method for Electric Parametric Characterization and Optimization of Electroporation on a Chip," Analytical Chemistry, vol. 85, No. 9, Apr. 2, 2013, 9 pages.

* cited by examiner

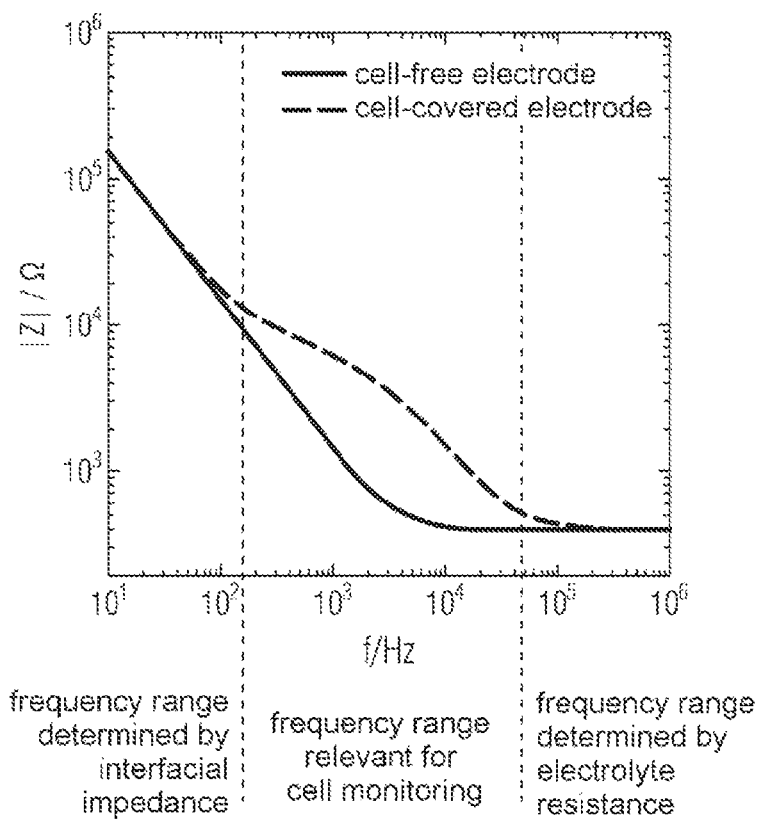
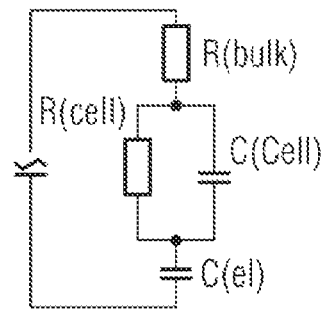
FIG. 1A
FIG. 1B
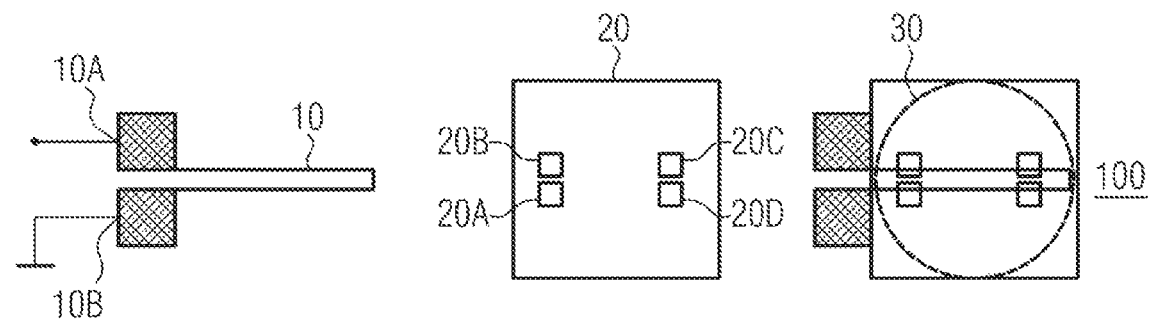
FIG. 2A  FIG. 2B  FIG. 2C

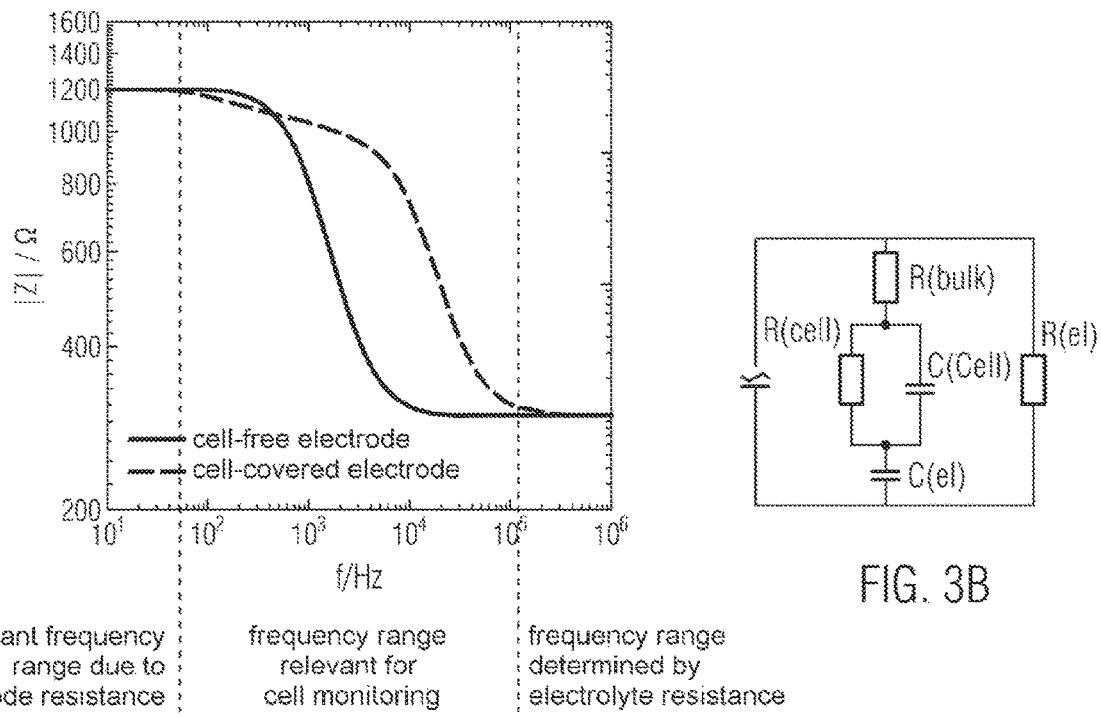
FIG. 3B
FIG. 3A
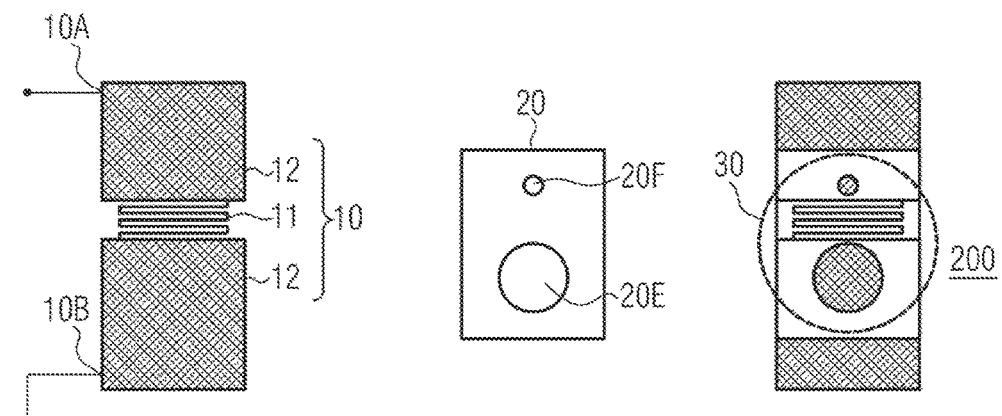
FIG. 4A        FIG. 4B        FIG. 4C

BIPOLAR ELECTRODE FOR THE IMPEDIMETRIC EXAMINATION AND MANIPULATION OF LIVING CELLS IN VITRO

CROSS REFERENCE TO RELATED APPLICATION

This application claims priority to German Patent Application No. 10 2016 224 865.0 entitled "BIOPOLAR [SIC] ELECTRODE FOR THE IMPEDIMETRIC EXAMINATION AND MANIPULATION OF LIVING CELLS IN VITRO," filed on Dec. 13, 2016, the entire contents of which are incorporated herein by reference for all purposes.

TECHNICAL FIELD

The present disclosure relates generally to measuring devices and their components for use in impedance sensing of adherent cells that are cultivated on electrically conductive substrates (electrodes). In particular, the present disclosure relates to an electrode array, a measuring device using this electrode array, and various uses of this electrode array.

BACKGROUND

Electrical cell substrate impedance sensing is described, for example, in international patent applications WO 2013/012498 A1 and WO 2016/139566 A1. Electrical impedance sensing of cells adherently growing on electrically conductive substrates (electrodes), referred to hereinafter as ECIS (electric cell substrate impedance sensing), is known as a label-free, impedance-based real-time method for examining the activity of living cells in vitro, i.e. cell cultures grown outside a living organism in a controlled laboratory environment. The method is based on cultivating cells on a planar gold film electrode, e.g. in a Petri dish. The impedance between the cell-covered gold film electrode and a counter electrode is measured at one or more frequencies as a function of time. By recording time- and frequency-resolved impedance measurements, the growth of the cell layer, cell shape changes, changes in the permeability of the cell membrane, and the like can be recorded. Such recordings and measurements can be used, for example, in drug and cytotoxicity screening. Furthermore, the cells can also be manipulated using the electrodes. By applying voltage pulses, the cells can be perforated to increase the permeability of the cell membrane for certain substances/drugs, so that the cell reaction under the influence of these substances can be observed impedimetrically and/or optically. For optical measuring, a fluorescence microscope with an upright stand and a waterproof immersion objective is typically used due to the opaque gold film electrode. With suitable voltage pulses, the cells on the electrode can also be killed in order to subsequently investigate the regeneration/healing of the damage.

ECIS has some technical limitations that have been insufficiently solved in prior art. The following outlines these issues and their current solutions.

Impedance Analysis

For impedimetric examination of living adherent cells (ECIS), two coplanar gold film electrodes are typically used, between which a constant alternating voltage is applied. One example of the method and device can be found, for example, in Wegener, J. "Electric Cell Substrate Impedance Sensing (ECIS) as a Noninvasive Means to Monitor the Kinetics of Cell Spreading to Artificial Surfaces", published in "Exp. Cell Res". 259, 158-166 (2000). A low amplitude of the voltages and currents applied ensures that the sensing itself has no influence on the cells. The current flows from one electrode through the cell layer via the electrolyte to the counter electrode. A small working electrode and a much larger counter electrode or else two equally sized working electrodes are generally used, so that the measuring signal is determined through the cell layer as best as possible.

FIG. 1A shows, as an example of a prior art ECIS measurement, the impedance spectrum of MDCK-II cells (Madin-Darby canine kidney epithelial cells) with an electrode and a counter electrode made of gold film. The low-frequency range is determined only by the interfacial capacitance of the electrodes and contains little analytically relevant information.

FIG. 1B shows a simplified equivalent circuit diagram of a cell layer on such an electrode array. R(cell) denotes the resistance of the cell layer, C(cell) denotes the capacity of the cell layer, C(el) denotes the interfacial capacity of the electrode and R(bulk) denotes the electrolyte resistance.

Due to the interfacial capacitance of the electrode, a typical frequency spectrum arises with increasing impedance at lower frequencies (see FIG. 1A). The spectra of the cell-free and cell-covered electrodes there hardly differ and the impedance is predominantly determined by the capacitance at this interface. As shall be described below, no analytically relevant information is obtained, inter alia, for technical measurement reasons. At frequencies below 10 Hz, impedance values above $10^7 \Omega$ can be obtained, depending on the electrode size. At these impedance values, the currents are correspondingly low due to the exclusive use of small voltage amplitudes. These low currents can only be reliably resolved with very accurate and expensive measuring devices, so that frequency spectra with commercial devices often show high levels of noise at low frequencies.

Low frequencies below 100 Hz have previously hardly been used to study the cell layer and, instead, are used mainly in describing the electrochemical parameters of the cell-free electrode required for the overall description of the system. Since this low frequency range is very susceptible to interference and is noisy due to the high load impedances, this part of the analysis is often neglected or bypassed by approximation methods. For example, the impedance spectra in this frequency range are either not measured at all, or the measurement of the spectra does not begin until 10 or 25 Hz, so that noise at smaller frequencies is bypassed. The companies listed below are the principal commercial providers of measuring systems for impedimetric analysis of adherent cells: Applied BioPhysics Inc. (Troy, N.Y.: www.biophysics.com), Acea Bioscience Inc. (San Diego, Calif.: www.aceabio.com), nanoAnalytics GmbH (Munster, www.nanoanalytics.de) and nanion (Munich, www.nanion.de).

Gold has been used almost exclusively as electrode material because it is best suited due to (i) its chemical inertness, (ii) outstanding biocompatibility, (iii) well-developed wet-chemical lithography, and not least due to (iv) good electrochemical descriptiveness. The layer thicknesses of the gold electrodes at >100 nm for impedimetric sensing are large enough to be able to neglect their inherent resistance. The large thickness of the gold film electrodes contributes significantly to the production costs of the gold electrodes as well as to their more difficult use in the simultaneous microscopic examination of the cells on the electrodes.

In summary, this means that the electrode array according to prior art in commercial measuring systems is expensive and limiting for simultaneous optical cell monitoring. Furthermore, the electrode arrays currently employed are difficult to use for impedance spectroscopic characterization at low frequencies.

Temperature Measurement

ECIS measurements are used to study live mammalian cells and must therefore be conducted in an incubator at constant 37° C. However, when changing the culture medium (nutrient solution) or when adding a substance whose influence on the cells is to be investigated, the incubator must typically be opened so that heat exchange with the environment takes place. Also, the solution added is often not exactly 37° C. even after preheating, since it can have cooled down again, for example due to the cooler temperature of a pipette tip. Such temperature fluctuations are reflected in the measurement readings, can influence the cell response, and must therefore be taken into account in the evaluation.

Temperature measurements in the immediate micro-vicinity of the cells examined have previously not been known in the context of impedance-based cell analysis. In general, the temperature is set for the incubator and establishment of an equilibrium is then awaited. Only the electrolyte resistance (impedance at very high frequencies) can be used as an approximation for temperature monitoring. The temperature influence on the outcome of the measurement is to be kept as low as possible by preheating the solutions to be investigated and opening the incubator for the shortest possible periods of time during the addition. However, resistive temperature sensors are known which are integrated in microfluidic chips and must be controlled separately for temperature measurement. Such resistance thermometers, like e.g. the platinum measuring resistor Pt1000, are also used in the industry due to their linear temperature dependence.

In summary, this means that temperature effects can hardly be taken into account at present with the conventional, impedance-based analysis of adherent cells. On-chip temperature sensor approaches, however, require an additional manufacturing effort for additional structures on the growth surface functionalized with the electrode array, which are often designed as disposables. This approach of separate integration of temperature sensors would therefore lead to higher manufacturing costs.

Electroporation and Electrical Wounding

Another field of application arising from the cultivation of adherent cells on gold film electrodes is electroporation of cell membranes. The membranes of living cells form a selective, semi-permeable membrane and prevent large and hydrophilic molecules and ions from diffusing in and out. In many fields of cell biology and biomedical research, however, applications are often in demand in which such non-membrane-passing molecules such as peptides, antibodies, nucleic acids, pharmaceuticals, or fluorescent dyes for molecular recognition are precisely to be introduced into the cell. In electroporation, short voltage pulses of sufficiently high amplitude and pulse duration are applied to reversibly permeabilize the cells for a particular molecule. The corresponding ancillary conditions, such as the concentration of the molecules to be introduced, the pulse duration, the number of pulses and the pulse amplitude must be adapted to the respective cell type and molecule. Due to the large number of parameters, the optimization can consume a significant amount of time.

If the same amplitudes are applied over a longer period of time (10-180 s) instead of short voltage pulses in the millisecond range, then the cells on the electrode are irreversibly permeabilized and thereby killed. Thereafter, the regeneration of the cell layer can be monitored in a time-dependent manner via the change of the impedimetric signal. These so-called wound healing assays depend on the same parameters as electroporation and also require elaborate optimization steps.

The optimization of electroporation or wounding with various discrete parameter combinations is generally carried out successively, each in a single so-called "wells" of, for example, microtiter plates. The cell response can be read out by subsequent impedance sensing, while the degree of loading with a fluorescent dye is determined by fluorescence microscopy. Due to the large number of parameters, an electroporation method, which allows pulsing in a single experiment in a measuring chamber at different amplitudes, can achieve an enormous time advantage. Attempts to accelerate the optimization of electroporation by way of voltage gradients can already found in literature, for example in Granot, Y. & Rubinsky, B. in "Methods of optimization of electrical impedance tomography for imaging tissue electroporation", published in "Physiol. Meas". 28, 1135-1147 (2007). This document discloses imaging and mathematical modeling of the electric field around two electrodes during electroporation. This method can two-dimensionally resolve the lateral electrical conductivity of the cells in tissue, but is very complex and requires a plurality of electrodes for imaging. Microscopic examinations are not possible there.

Kim, J. A. et al. in the article "A multichannel electroporation microchip for gene transfection in mammalian cells", published by "Biosens. Bioelectron". 22, 3273-3277 (2007) describe the use of parallel microfluidic channels of different lengths, so that different electric field strengths are generated when applying a voltage between input and output. In this case, however, the cells are suspended in the solution and not on the substrate.

Wu, M. et al. in the article "Method for Electric Parametric Characterization and Optimization of Electroporation on a Chip", published by "Anal. Chem." 85, 4483-4491 (2013) describe specific electrode structures that create a voltage gradient between two electrodes.

The latter two techniques are limited to performing electroporation, but do not provide any integrated analytics option and, cannot be combined with impedance sensing. All these methods mentioned have the drawback that very high DC voltages of several hundred volts are used for electroporation, where electrochemically reactive and cytotoxic molecular species are typically generated at the electrode surface in physiological buffers.

Fluorescence Microscopy

In cell biological applications, it is often demanded that a fluorescence microscopic examination of the cells on an electrode be performed in parallel, for example when fluorescent markers have been introduced into the cell during electroporation. However, the typical thicknesses of the gold film electrodes of 50 to 100 nm are too thick for the very advantageous inverted microscopes commonly used in cell biology and have too low a transmission at the relevant wavelengths. The relatively low-intensity fluorescent light cannot penetrate the gold films, so that upright microscopes commonly need to be employed. However, upright microscopes allow a small working distance to the object only with additional effort and require special immersion objectives. In principle, the use of transmitted light microscopy is also possible only to a very limited extent because of the low transparency of the conventional gold film electrodes.

Since the detection of fluorescent light cannot be done from below due to the gold layer being opaque, upright microscopes must be used. In order to approach the objective close enough to the cell, it is therefore necessary to first remove the chamber of the electrode array. This is very complex and involves the risk of destruction of the cell layer or some other impairment of the measurement. Alternatively, the use of the electrically conductive and in thin layers translucent material indium tin oxide (ITO) was described in the literature as electrode material. However, due to its rarity, ITO is becoming increasingly expensive and corrodes more easily than gold, which becomes particularly relevant at the higher voltage amplitudes required for electroporation.

One or more of the limitations explained above are eliminated with the present disclosure. In one aspect, it is an object of the present disclosure to provide a device with which electrical (impedimetric) examinations of adherent cells are possible in a simple manner while simultaneously detecting the temperature in the medium measured.

A further object of the present disclosure is to provide a device which simultaneously allows electrical (impedimetric) and optical (microscopic) examinations and which permits the use of inverted microscopes which approach the object from the back side of the cell culture substrate, i.e. on the dry side.

BRIEF SUMMARY OF THE PRESENT DISCLOSURE

The above object is satisfied by a bipolar electrode array which is adapted for being wetted with an electrolyte solution and adherently growing cells in order to perform impedimetric cell analysis, characterized in that the electrode array comprises a bipolar electrode (10) on a substrate, where the bipolar electrode (10) is formed as a conductive path on the transparent substrate and has an inherent resistance between two connection points (10A, 10B) of the conductive path that is a multiple of the AC impedance of the electrolyte solution at 1 MHz, measured at the two connection points (10A, 10B).

In a bipolar electrode, the anode and the cathode are at the same time disposed in a continuous conductive film due to the relatively high inherent resistance of the bipolar electrode. The high inherent resistance of the continuous conductive film necessary for the functionality is enabled by the use of very thin and thus transparent layers as electrodes. The temperature dependence of the inherent resistance of these bipolar electrodes allows determining the temperature directly beneath the cell layer simultaneously during the impedance examination on the cells. This method therefore offers the possibility to calculate temperature effects. By adjusting the resistance and the shape of the bipolar electrode, the electrode array can further be adapted to different measurement circumstances, such as the cell type, the electrolyte type, the frequency range of interest during impedance spectroscopy and the like, and to the objective of the examination such as cell growth, wound healing, determination of the optimal electroporation voltage and the like.

In one embodiment, the substrate and the conductive path are transparent, at least in a measurement range intended for adherent cells.

If such an electrode array (bipolar electrode) is generated on an optically transparent substrate (e.g. microscope slide, glass cover), the cell cultures growing on the continuous conductive film (bipolar electrode) are accessible to transmitted light microscopy and inverted fluorescence microscopy from the dry back side of the substrate (microscope slide, glass cover).

In one embodiment, the bipolar electrode is a film electrode made of gold, indium tin oxide (ITO), conductive polymers, such as polyaniline, polypyrrole, polythiophene, PEDOT or their doped and/or chemically modified variants.

Materials such as glass, polycarbonate, polyethylene, terephthalate (PET), polyethylene naphthalate (PEN) or a porous membrane, for example made of a biocompatible plastic material, are suitable as a transparent substrate.

The materials mentioned for the transparent substrate and the bipolar electrode are, at the required thicknesses, both transparent as well as biocompatible with living cells with which the examinations are to be conducted.

Alternatively, the porous membrane can be nontransparent where a microscopic transmitted light examination is not required, for example, where only impedance sensing is to be conducted on how the adherent cells behave when they are supplied with nutrients and/or active substances predominantly from the back side of the substrate through the pores or also from both sides.

In one embodiment, the bipolar electrode is a gold film with a layer density in the range of 10 nm to 30 nm, preferably in the range of 20 nm±2 nm. At a layer thickness in the range of 20 nm, gold is optically transparent, chemically inert and almost ideally polarizable i.e. no charge transfer occurs on the gold surface. Furthermore, gold is easy to structure with known lithographic methods and functionalized with self-assembly techniques.

In one embodiment, the bipolar electrode has an inherent resistance of at least 300 ohms, preferably at least 600 ohms, more preferably at least 1200 ohms. The high inherent resistance leads to a gradual voltage drop between different points of the electrode, so that a bipolar electrode is created in which the anode and the cathode are simultaneously present on the continuous film. Furthermore, experimental arrangements can be designed in which trials at different voltages through the voltage gradients along the film are conducted at the same time. This allows trials to be conducted in a more time-efficient manner.

However, these values only apply to certain embodiments with highly transparent electrodes. Other embodiments are also conceivable in which smaller inherent resistances are also sufficient, for which the transparency is then increasingly reduced, but sensing still remains possible.

In a further embodiment, the bipolar electrode may further comprise at least one elongate narrow region having a length that is at least ten times the width. By reducing the cross section, a required resistance value can be obtained. Depending on the application, the elongate narrow region can be formed in some embodiments to have a U-shape, an L-shape or a meandering shape. By forming a U-shape, an L-shape or a meandering shape, very elongate narrow regions can also be arranged on a chip in a space-saving manner.

In an additional embodiment, the bipolar electrode may comprise at least one planar region which has a length that is less than ten times the width. With the large-area region, larger regions with an approximately constant potential can be realized, with which the impedance signal is integrated over a larger area, for example, for monitoring the growth of a biofilm. In combination with an elongate narrow region of the bipolar electrode, the planar region can also serve as a counter electrode with a constant potential compared vis-à-vis several measuring regions on the elongate narrow region, in which the cells are exposed to different voltages depending on the position on the narrow elongate region.

In another embodiment, the electrode array may comprise an insulating layer covering the bipolar electrode and having at least two recesses at defined locations above the bipolar electrode to enable electrical communication between the recessed electrode regions via the electrolyte. The recesses create defined measuring ranges to which a defined area and a defined voltage can be assigned, so that more defined ancillary conditions can be created for impedance sensing.

In one embodiment, the electrode array further comprises a boundary above the bipolar electrode, with which a measuring chamber is defined. The boundary ensures that the electrolyte solution can only wet the intended regions on the electrode array and prevents the electrolyte solution from reaching, for example, the connection pads, thus leading to falsified impedance sensing.

In one embodiment, the boundary is made of material that is compatible to cell cultures, preferably of glass or polystyrene.

In another embodiment, the film electrode was photolithographically structured in a wet-chemical etching process. In this way, precise and fine electrode structures can be realized in an inexpensive manner.

In another aspect, the present disclosure relates to a measuring device comprising a support device adapted to hold a chip with a bipolar electrode array. The measuring device further comprises an impedance analyzer which is electrically connectable to the bipolar electrode array, and a microscope, such as, but not limited to, a fluorescence microscope, which is arranged such that a cell culture on the bipolar electrode array can be examined with the microscope from the dry back side of the carrier substrate (microscope slide, glass cover). With such a measuring device, impedimetric and microscopic examinations of cell cultures can be conducted simultaneously, where the microscope objective can be arranged at the dry back side of the chip, i.e. no special immersion objectives are needed. A small working distance to the objective can thus be obtained without much effort. In addition, the use of a bipolar electrode array for measurements in transmitted light allows for better illumination and thus for higher-contrast imaging of the cell cultures. This makes it possible to use inverted microscopes which are widespread and advantageous in cell biology. Furthermore, it is possible to examine cells simultaneously with such a measuring device at several voltages, whereby the effort for several preparations for examinations at different voltages is saved.

In a further aspect, the disclosure relates to the use of a measuring device with an integrated bipolar electrode array for simultaneous impedimetric and microscopic examination of living cells.

In yet another aspect, the present disclosure relates to the use of the bipolar electrode array for electroporation and/or electrical wounding of adherent cells, e.g. with the aim of examining the healing of the wounded cells. Cell membranes can be reversibly perforated with the bipolar electrode so that selected substances can be introduced into the cell. The effect of the substances can then be examined in a subsequent impedimetric and microscopic examination on the electrode array. Similarly, cells can be selectively killed, so that the regeneration of the cells can then be monitored in the subsequent impedimetric and microscopic examination. Furthermore, the optimal voltage for electroporation can be determined in one measurement run, since measurements at different voltages can be conducted simultaneously due to the voltage gradients along the bipolar electrode.

BRIEF DESCRIPTION OF THE FIGURES

Embodiments, further developments, advantages and possible applications of the disclosure shall be explained in more detail below with reference to the appended figures. All features described and/or illustrated there are by themselves or in random combination basically the object of the disclosure, regardless of their combination in the claims or their relation. The content of the claims is also made part of the description.

FIG. 1A shows an impedance spectrum of a confluent cell layer on a gold film electrode according to prior art in comparison to the same but cell-free electrode.

FIG. 1B shows a simplified equivalent circuit diagram of a cell layer on a gold film electrode according to prior art.

FIG. 2A shows the structure of a planar bipolar electrode according to an embodiment of the present disclosure.

FIG. 2B shows the structure of an optional insulating photoresist layer applied over the bipolar electrode according to an embodiment of the present disclosure.

FIG. 2C shows the overall structure of an embodiment according to FIGS. 2A and 2B.

FIG. 3A shows an impedance spectrum of a bipolar electrode according to the present disclosure in comparison to the same but cell-free electrode.

FIG. 3B shows a simplified equivalent circuit diagram of a cell layer on a bipolar electrode according to the present disclosure.

FIG. 4A shows the structure of a planar bipolar electrode according to an embodiment of the present disclosure.

FIG. 4B shows the structure of an optional insulating photoresist layer applied over the bipolar electrode according to an embodiment of the present disclosure.

FIG. 4C shows the overall structure of the second embodiment according to FIGS. 4A and 4B.

DETAILED DESCRIPTION

Figure 5A:
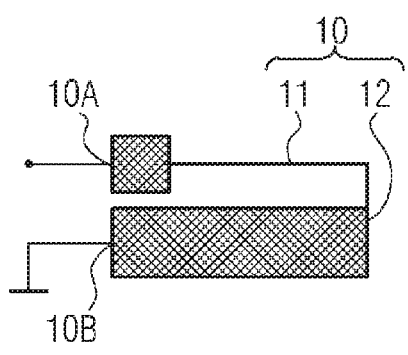
FIG. 5A shows the structure of a planar bipolar electrode according to an embodiment of the present disclosure.

This disclosure provides a novel continuous potential gradient bipolar film electrode that enables label-free and time-resolved impedance analysis of adherent cells. Depending on the selection of the electrode material, the dielectric properties of the cells and the temperature in the immediate vicinity of the cells can be detected directly from the impedance spectrum. The measurement can be combined with gradual electroporation of the cells with simultaneous microscopic monitoring. The general principle of the disclosure and some applications shall be described below.

The Principle of the Present Disclosure

The present disclosure consists essentially of a transparent substrate, such as glass, polycarbonate, PET (polyethylene terephthalate), or PEN (polyethylene naphthalate), which is coated with conductive electrode material with sufficiently high inherent resistance, so that a significant resistance of at least several hundred ohms arises between the two contact points to an external voltage source. The electrode material must have a very small layer thickness and/or a long conduction length and/or a high specific resistance in order to ensure the high resistance. The film electrode can be made of gold, indium tin oxide (ITO), or conductive polymers, such as e.g. polyaniline, polypyrrole, polythiophene, PEDOT, and their doped and chemically modified variants. The high inherent resistance leads to a gradual voltage drop between the contact points of the electrode to an external voltage source so that a bipolar electrode (anode and cathode simultaneously in a continuous metal film) is formed. A current flow can now take place between the poles of the bipolar electrode not only through the electrode film but also via the cells growing on the electrode and the electrolyte disposed thereabove. The impedance spectrum of this arrangement then, in addition to the resistive properties of the electrode material, also contains information about the dielectric properties of the cells.

Basic Structure

FIG. 2 generally shows a structure of a bipolar electrode array 100 with several components. FIG. 2A shows a planar bipolar electrode 10, for example, in the form of a gold foil electrode after photolithographic structuring on a transparent substrate (not shown). The larger regions with connection points 10A and 10B are used to connect to the measuring electronics. FIG. 2B shows the structure of an optional insulating photoresist layer 20 that can be applied onto electrode 10. Recesses 20A, 20B, 20C and 20D define the effective electrode size and its electrical potential. FIG. 2C shows a superposition of electrode 10 and insulator layer 20, as well as boundary 30 of the measuring chamber (dashed line).

If the resistance of the film electrode is too low, then the electrode causes only a short circuit and measurement of the cells is no longer possible. Gold is optically transparent, chemically inert and almost ideally polarizable at a layer thickness in the range of 20 nm. Thin layers can be photolithographically structured with an iodine/potassium iodide solution by wet-chemical etching.

FIG. 2C, by way of example, shows the configuration of a measuring chamber with a bipolar gold film electrode after fabrication in several steps. The surfaces outside the measuring chamber are used for connecting to the measuring electronics and are kept relatively large in area to minimize the lead resistance. In contrast, the internal structure, on which the cells are disseminated, is designed for a suitable intrinsic resistance and is therefore narrow and long. Since the bulk resistance of the electrolyte also has an influence on the sensitivity of the measurement, it must be kept low, which is why the two parallel strands of U-shaped electrode 10 are disposed very close to each other. Depending on the application, electrode 10 is coated with an insulator layer 20 made of a photoresist, which contains two or more photolithographically defined recesses 20A, 20B, 20C, and 20D for electrodes 10. The measuring chamber then has only one electrode 10, but various defined potentials effectively arise at the various locations of recesses 20A, 20B, 20C and 20D of electrode 10 for a voltage U applied from the outside, and thus potential differences U between two different locations, for example, between recesses 20A and 20B on electrode 10. This voltage between the electrode locations induces a parallel current flow across the adherent cells, which is determined by the dielectric properties of the cells and makes them measurable. U depends on the resistance of the electrode material R(el) between the positions of the exit and entry points of the electric current and indicates the voltage dropping thereacross. By using an insulator layer, U can be discretely defined, while otherwise a continuous potential gradient would be given.

The boundary of the measuring chamber is made of material suitable for the cell culture, such as glass or polystyrene. Prior to the cells being disseminated into the measuring device prepared, the latter is incubated with a cell medium. Adherence and spreading of the cells on the electrode can be monitored impedimetrically.

Impedance Spectroscopy

The impedance analysis is conducted by way of an impedance analyzer by applying an alternating voltage or an alternating current with a low, non-invasive amplitude. The impedance spectra of the bipolar electrode array at high frequencies hardly differ from those observed using conventional prior art pairs of electrodes, but at low frequencies are not affected by the interfacial capacitance of the electrode but dominated by the inherent resistance of the electrode R(el) (see FIG. 3).

FIG. 3A shows an impedance spectrum of a confluent layer of MDCK-II cells measured with a bipolar electrode according to the present disclosure in comparison to the impedance spectrum of the same, but cell-free electrode. The low-frequency range is determined by the inherent resistance of the electrode and can be used, for example, to determine the temperature beneath the cell layer.

FIG. 3B shows a simplified equivalent circuit diagram of a cell layer on a bipolar electrode according to the present disclosure. R(cell) denotes the resistance of the cell layer, C(cell) denotes the capacity of the cell layer, C(el) denotes the interfacial capacity of the electrode, R(bulk) denotes the electrolyte resistance, and R(el) denotes the inherent resistance of the electrode.

The maximum achievable impedance is therefore limited by the selection of the inherent resistance of the electrode. In this way, the frequency-independent minimum current be adjusted to the performance of the measuring device.

For quantitatively exact impedance analysis, the bipolar electrode array 200 uses a variant with an insulator layer as the electrode, which by way of its defined recesses determines the electrode surface necessary for determining surface-specific parameters (see FIG. 4).

FIG. 4A shows the structure of bipolar electrode 10 according to an embodiment of the present disclosure in the form of a planar gold electrode. Bipolar electrode 10 is divided into a narrow, elongate region 11 which is folded in a meandering shape, and larger-area regions 12 which are electrically connected to each other via the region of meandering shape.

FIG. 4B shows the structure of an insulating photoresist layer 20 which can be applied onto electrode 10 and whose recesses 20E and 20F define the size of the work and counter electrodes.

FIG. 4C shows the superposition of electrode 10 and insulator layer 20, as well as boundary 30 of the measuring chamber (dashed line).

The meandering structure ensures that the inherent resistance of the electrode is high enough.

Electroporation and Electrical Wounding

The continuous potential gradient of the electrode can be used in electroporation for time-saving optimization of the electroporation parameters. Instead of several measurements at different voltage amplitudes, a single one is sufficient in which the optimum amplitude can be read on the electrode with the best electroporation result from the position. The bipolar electrode array 300 uses an electrode without any further insulator layer in order to utilize the potential gradient in a stepless manner. Alternatively, an insulator layer with an electrode layout in the form of a photoresist can be applied in order to be able to pick up specific voltages in dependence of the position via recesses produced by photolithography (see FIG. 5).

FIG. 5A shows the structure of bipolar electrode 10 according to an embodiment of the present disclosure in the form of a planar gold electrode. As shown in FIG. 5A, bipolar electrode 10 may be divided into a narrow, elongate region 11, which is L-shaped, and a larger-area region 12.

Figure 5B:
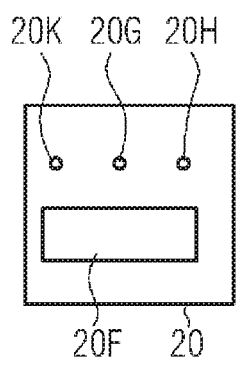
FIG. 5B shows the structure of an optional insulating photoresist layer applied over the bipolar electrode according to an embodiment of the present disclosure.

FIG. 5B shows the structure of an (optional) insulating photoresist layer 20 which can be applied onto electrode 10 with a large-area recess 20F defining the size of the counter electrode and three small-area recesses 20G, 20H and 20K whose diameter corresponds to approximately the width of narrow, elongate region 11 for defining the size and the electrical potential of three electroporation positions.

Figure 5C:
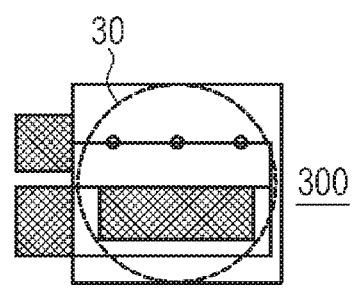
FIG. 5C shows the overall structure of an embodiment of the present disclosure according to FIGS. 5A and 5B.

FIG. 5C shows the superposition of electrode 10 and insulator layer 20, as well as boundary 30 of the measuring chamber (dashed line).

If one measures the impedance spectrum of a cell layer after electroporation with the same electrode array, then a signal averaged over all positions with an individual potential gradient is obtained. At the same time, the effect of electroporation can be verified with a microscope.

Temperature Measurement

In the constant range at low frequencies, the impedance depends exclusively on the inherent resistance of the gold electrode, which in turn depends on the temperature. Impedance changes in this frequency range are therefore to be attributed to a change in temperature, with all other experimental parameters being constant, so that temperature changes, after respective calibration, can be read directly from the temporal change of the impedance spectrum. Impedimetric examinations of cells with this method therefore have the ability to determine the temperature directly beneath the cell layer and bear the possibility of calculating temperature effects.

Fluorescence Microscopy

Gold is largely transparent to visible light at a layer thickness of 20 nm. Due to this fact, a bipolar electrode of the present disclosure is very well suitable for fluorescence microscopy with inverted microscopes. The thin electrode films allow the transmission also of low-intensity fluorescent light. The high internal resistance of the electrodes inevitably associated with the transparency is desirable—in contrast to the established techniques based on two electrodes. With the electrode structures currently commercially available, the use of an upright microscope, in which the objective must be approached to the cells from the top side over which the medium is layered, is laborious and impractical. In addition, special immersion objectives are needed. When using bipolar electrodes with very thin electrode thicknesses, electroporation or the electrical use can be monitored in parallel microscopy with an inverted microscope without breaching the sterility of the sample, as this does not require removal of the measuring chamber.

The use of bipolar thin-film electrodes entails significant advantages in the electrode fabrication, since significantly less electrode material (10%-20% of the amount conventionally applied) is needed and each etching step can be performed with fewer reagents and shorter etching times. Overall, a significant reduction in production costs is to be expected—mainly due to lower gold consumption.

The thinner film electrodes also allow parallel examination of the cells with microscopic techniques without breaching the sterility of the sample. Such a combination of optical and electrical examination methods provides, firstly, spatially resolved information about individual cells and, secondly, integral statements about the physical behavior of a cell group. Each electrical measurement or manipulation can be monitored optically in parallel without any problems and with inverted microscope optics.

With exact manufacturing of the electrode structure and thus more accurate specification of the internal resistance of the electrode, the measurement range in an impedance spectrum to be tolerated is highly narrowed in a well-defined manner and thus enables avoiding the very high-impedance sensing points at low frequencies. In this way, very accurate adaptation of the measuring electronics to the relevant load impedances is possible without limiting the frequency range.

The use of bipolar electrodes provides a significant time gain in the optimization of experimental parameters for electroporation or wounding experiments. By exploiting flowing potential gradients, the amplitude dependence of the voltage pulses applied is detected in an experiment.

The constant range of the impedance spectrum at low frequencies delivers a measurement that is correlated with the temperature in direct proximity to the cells.

The invention claimed is:

1. An electrode array adapted for being wetted with an electrolyte solution and for adherently growing cells in order to perform impedimetric cell analysis comprising:
    a bipolar electrode on a substrate,
    wherein said bipolar electrode is formed as a conductive path on said substrate;
    wherein said bipolar electrode has an inherent resistance between two connecting points of said conductive path which is a multiple of an AC impedance of said electrolyte solution at 1 MHz, as measured at said two connecting points, wherein said two connecting points are configured to be connected with an impedance analyzer and receive an alternating voltage or an alternating current with a low, non-invasive amplitude; and
    wherein an anode and a cathode of the bipolar electrode are at the same time disposed in a continuous conductive film representing the conductive path due to the resistance of the bipolar electrode being high.

2. The electrode array according to claim 1, wherein said substrate and said conductive path are transparent in a measuring region intended for adherent cells.

3. The electrode array according to claim 2, wherein said transparent substrate is glass, polycarbonate, polyethylene terephthalate (PET), a porous membrane, or polyethylene naphthalate (PEN).

4. The electrode array according to claim 1, wherein the inherent resistance of said bipolar electrode is at least 300Ω.

5. The electrode array according to claim 1, wherein said bipolar electrode is a gold film with a layer thickness between 10 nm to 30 nm.

6. The electrode array according to claim 1, wherein said bipolar electrode comprises at least one elongate narrow region having a length that is at least ten times a width.

7. The electrode array according to claim 6, wherein said elongate narrow region is U-shaped, L-shaped, or of a meandering shape.

8. The electrode array according to claim 1, wherein said bipolar electrode comprises at least one planar narrow region having a length that is less than ten times a width.

9. The electrode array according to claim 1, further comprising an insulating layer covering said bipolar electrode and comprising at least two recesses at defined locations above said bipolar electrode.

10. The electrode array according to claim 1, further comprising a boundary above said bipolar electrode with which a measuring chamber is defined.

11. The electrode array according to claim 10, wherein said boundary is made of material that is compatible to cell cultures.

12. The electrode array of claim 1, wherein said bipolar electrode is a film electrode made of gold, indium tin oxide (ITO), conductive polymers, polyaniline, polypyrrole, polythiophene, PEDOT, or their doped and/or chemically modified variants.

13. A measuring device for impedimetric cell analysis comprising:
- a support device holding a chip with an electrode array on a transparent carrier material wherein the electrode array comprises a bipolar electrode on a substrate adapted for being wetted with an electrolyte solution and for adherently growing cells in order to perform the impedimetric cell analysis, wherein an anode and a cathode of the bipolar electrode are at the same time disposed in a continuous conductive film representing the conductive path due to a high inherent resistance of the bipolar electrode;
- an impedance analyzer which is electrically connectable to two connecting points of said electrode array; and
- a fluorescence microscope arranged such that a cell culture on said electrode array can be examined from a back side direction of said chip with said fluorescence microscope and an electrical measurement or manipulation can be monitored optically in parallel;
- wherein said bipolar electrode is formed as a conductive path on said substrate; and
- wherein said bipolar electrode has an inherent resistance between two connecting points of said conductive path which is a multiple of an AC impedance of an electrolytic solution at 1 MHz, as measured at said two connecting points.

14. The electrode array of claim 11, wherein the boundary is glass or polystyrene.

15. The electrode array of claim 1, wherein said bipolar electrode has an inherent resistance of at least at least 600 Ω.

16. The electrode array of claim 1, wherein said bipolar electrode has an inherent resistance of at least 1200 Ω.

17. The electrode array according to claim 12, wherein said film electrode was photolithographically structured in a wet-chemical etching process.

* * * * *